United States Patent

McNichols et al.

Patent Number: 6,090,095
Date of Patent: *Jul. 18, 2000

[54] ELECTROTRANSPORT DELIVERY DEVICE

[75] Inventors: Larry A. McNichols; John D. Badzinski, both of Coon Rapids, Minn.; Ronald P. Haak, Menlo Park, Calif.

[73] Assignee: ALZA Corporation, Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/881,529

[22] Filed: Jun. 24, 1997

Related U.S. Application Data

[63] Continuation of application No. 08/353,036, Dec. 8, 1994, Pat. No. 5,697,896.

[51] Int. Cl.[7] ............................................. A61N 1/30

[52] U.S. Cl. .................................... 604/501; 604/20

[58] Field of Search ............................ 604/20–21, 501; 607/62–63

[56] References Cited

U.S. PATENT DOCUMENTS 4,141,359  2/1979  Jacobsen et al. .
4,931,046  6/1990  Newman .

FOREIGN PATENT DOCUMENTS 0092015  10/1983  European Pat. Off. .

*Primary Examiner*—Mark Bockelman
*Attorney, Agent, or Firm*—Owen J. Bates; Steven F. Stone; D. Byron Miller

[57] ABSTRACT

An electrotransport delivery device (410) includes control circuitry for discontinuously delivering a beneficial agent (eg, a drug) through a body surface (eg, skin 400). For example, the device may be the type which is manually activated by the patient or other medical personnel to activate electrotransport drug delivery. Once electrotransport delivery has been activated, a timer (221) counts a transition interval, typically about one minute, during which the device is allowed to operate and the impedance of the body surface (400) is allowed to stabilize. Thereafter, the electrotransport current and voltage are then monitored and compared to predetermined limits. Allowing for the transition interval permits tighter tolerances in monitoring the applied current.

10 Claims, 9 Drawing Sheets

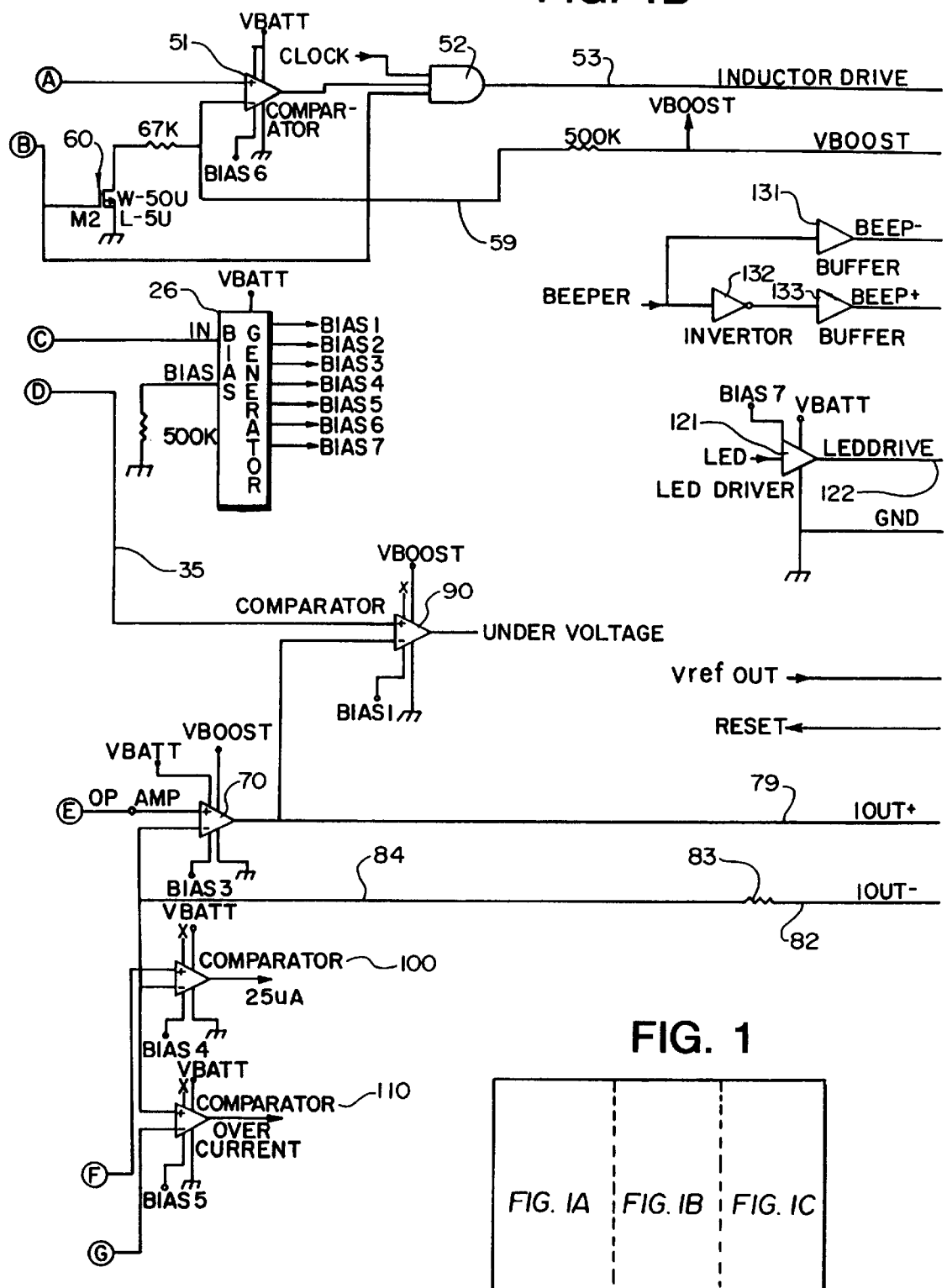
FIG. 1B
FIG. 1
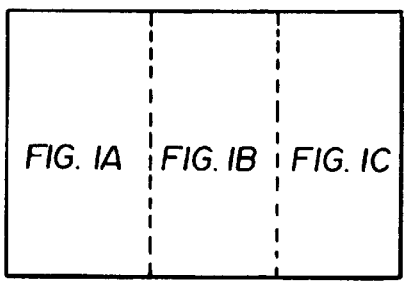

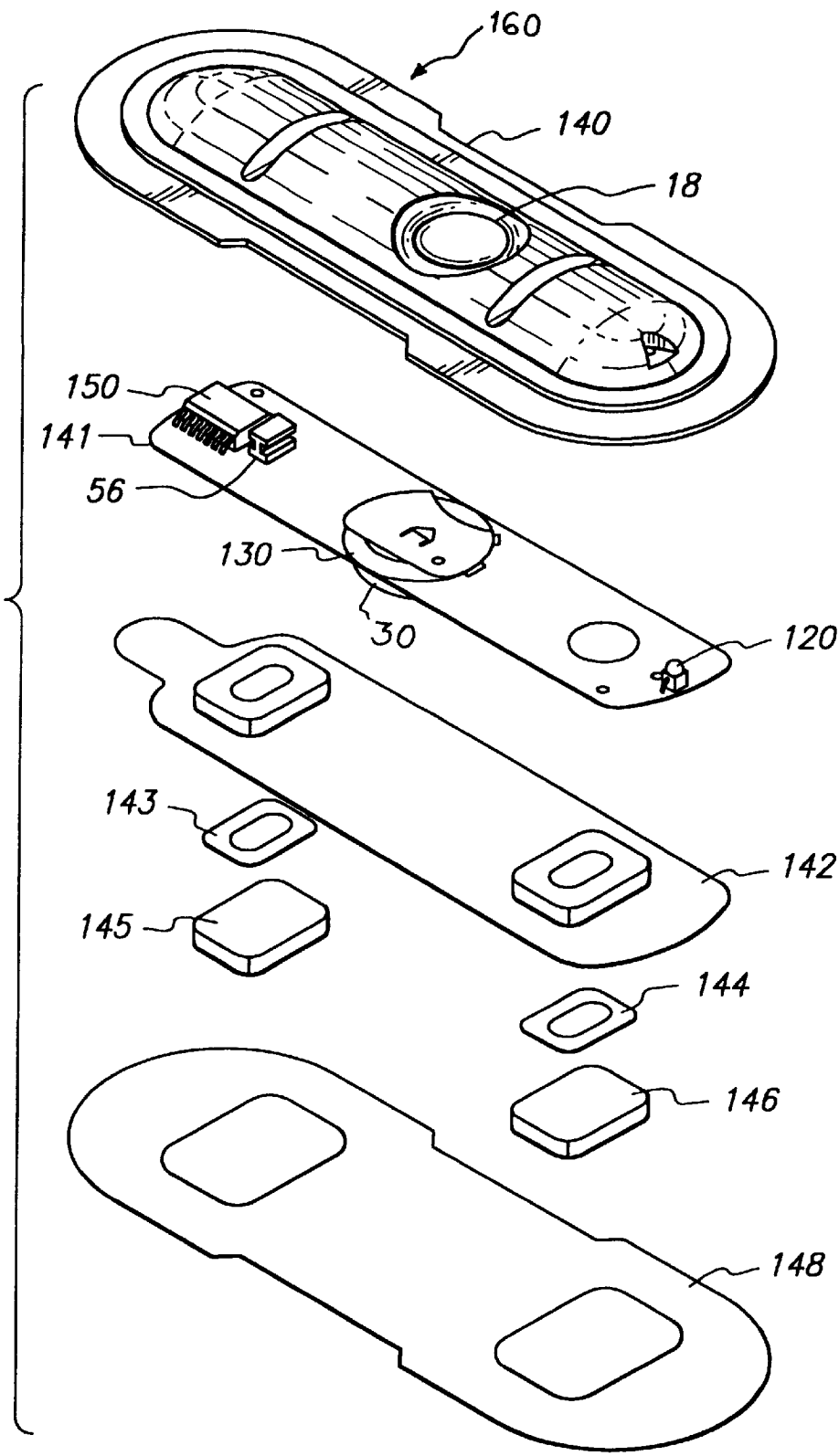

ELECTROTRANSPORT DELIVERY DEVICE

RELATED APPLICATIONS

This application is a continuation of application Ser. No. 08/353,036, filed Dec. 8, 1994 now U.S. Pat. No. 5,697,896, and benefit of the filing date of said earlier filed application is claimed under 35 USC § 120.

TECHNICAL FIELD

The present invention relates to a device and method of delivering a beneficial agent (eg, a drug) by electrotransport through a body surface. More particularly, the invention pertains to techniques for improved control over the electrotransport delivery.

BACKGROUND OF THE INVENTION

One type of transmembrane agent delivery is electrotransport, ie, electrically assisted transmembrane delivery. "Electrotransport" refers generally to the passage of a substance through a body surface or membrane, such as skin, mucous membranes, or nails, at least partially induced by the passage of an electrical current. For example, a therapeutic agent may be introduced into the human body by electrotransport. One widely used electrotransport process, iontophoresis, involves the electrically induced transport of charged ions. Electroosmosis, another type of electrotransport, involves the movement of a liquid through a biological membrane (eg, skin) under the influence of an electric field. Another type of electrotransport, electroporation, involves the transport of an agent through transiently-existing pores formed in a biological membrane under the influence of an electric field. In any given electrotransport process, however, more than one of these processes may be occurring simultaneously to a certain extent. Accordingly, the term "electrotransport", is used herein in its broadest possible interpretation so that it includes the electrically induced or enhanced transport of an agent, which may be charged or uncharged, or a mixture thereof, regardless of the specific mechanism(s) of transport.

More recently, a number of United States patents have issued in the electrotransport field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of electrotransport devices and some applications thereof. The electrotransport process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of electrotransport is in diagnosing cystic fibrosis by delivering pilocarpine salts by electrotransport. The pilocarpine stimulates sweat production; the sweat is collected and analyzed for its chloride content to detect the presence of the disease.

In presently known electrotransport devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by electrotransport. The other electrode, called the counter or return electrode, serves to close the electrical circuit through the body. In conjunction with the patient's skin contacted by the electrodes, the circuit is completed by connection of the electrodes to a source of electrical energy, eg, a battery. For example, if the ionic substance to be delivered into the body is positively charged (ie, a cation), then the anode will be the active electrode and the cathode will serve to complete the circuit. If the ionic substance to be delivered is negatively charged (ie, an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that electrotransport delivery devices can be used to deliver an uncharged drug or agent into the body. This is accomplished by a process called electroosmosis. Electroosmosis is transdermal flux of a liquid solvent (eg, the liquid solvent containing the uncharged drug or agent) which is induced by the presence of an electric field imposed across the skin by the donor electrode. As used herein, the term "electrotransport" applies equally to electrically powered devices which deliver charged/ionic agents by electromigration as well as to electrically powered devices which deliver uncharged/nonionic agents by electroosmosis.

Furthermore, existing electrotransport devices generally require a reservoir or source of the beneficial agent (which is preferably an ionized or ionizable agent or a precursor of such agent) to be delivered by electrotransport into the body. Examples of such reservoirs or sources of ionized or ionizable agents include a pouch as described in the previously mentioned Jacobsen U.S. Pat. No. 4,250,878, or a preformed gel body as described in Webster U.S. Pat. No. 4,382,529 and Ariura et al U.S. Pat. No. 4,474,570. Such drug reservoirs are electrically connected to the anode or the cathode of an electrotransport device to provide a fixed or renewable source of one or more desired agents.

More recently, electrotransport delivery devices have been developed which utilize complex electrical circuits in order to perform a number of functions. These complex circuits include pulsing circuits for delivering a pulsed current, timing circuits for delivering drugs over predetermined timing and dosing regimens, feedback regulating circuits for delivering drugs in response to a sensed physical parameter, and polarity controlling circuits for periodically reversing the polarity of the electrodes. See for example, Tapper et al U.S. Pat. No. 4,340,047; Lattin U.S. Pat. No. 4,456,012; Jacobsen U.S. Pat. No. 4,141,359; and Lattin et al U.S. Pat. No. 4,406,658.

Some electrotransport devices have used a simple DC power source, typically a battery, electrically connected in series with the two electrodes. See for example, Ariura et al, U.S. Pat. No. 4,474,570. Other devices have used more complex circuits to provide a current source for connection to the electrodes, and at least one of them (Jacobson et al, U.S. Pat. No. 4,141,359) proposes monitoring the electrical impedance of the skin contacted by the electrodes. A circuit monitors current flow and voltage across the electrodes and automatically triggers a shutdown circuit when impedance readings are outside predetermined limits, to thereby prevent excessive voltage build-up and the accompanying dangers of shock and burns. While the Jacobsen circuit is suitable for electrotransport devices which apply electric current continuously once activated, it is not well suited for electrotransport devices which apply electric current discontinuously once placed on the body and activated. Examples of electrotransport devices which discontinuously apply electric current to the patient include the device disclosed in Sibalis U.S. Pat. No. 5,013,293 (eg, electrotransport delivery of LHRH for 6 minutes out of every hour to mimic a normal healthy body's natural release of LHRH); electrotransport delivery of insulin before mealtimes; and patient-activated electrotransport delivery of pain killing agents (eg, narcotic analgesics) to control pain (eg, post-operative pain, chronic cancer pain, etc).

DISCLOSURE OF THE INVENTION

It has now been determined that body membrane (eg, skin) impedance goes through a normal change over a brief transition interval of time at the start of each new electrotransport treatment administered to the patient. In accordance with the present invention, body membrane (eg, skin) impedance, and/or related electrical parameters such as current and voltage drop, is checked after this transition time, making it possible to monitor the applied electrotransport current to tighter limits. The invention has particular utility in electrotransport devices which apply current discontinuously (eg, in an on-off fashion) such as those electrotransport devices which allow a certain degree of patient involvement in the use and control of an electrotransport drug delivery system, within limits that may be established by the manufacturer of the device or by the attending physician. For example, in the case of a pain medication being administered by electrotransport, it may be desirable to provide the drug delivery in short predetermined time intervals (ie, the device turns on for a short period of time and then turns itself off) which can be initiated by the patient, rather than by the device applying a predetermined level of current continuously.

The invention may optionally be implemented in conjunction with a lockout interval feature, to provide for patient initiated doses which run for a predetermined time, followed by a lockout interval during which treatment is prevented. This lockout interval can be preprogrammed to prevent too frequent dose administering.

BRIEF DESCRIPTION OF THE DRAWINGS

FIG. 3 is an exploded view of the mechanical assembly of an electrotransport delivery device with which the present invention can be used.

MODES FOR CARRYING OUT THE INVENTION

Figure 1A:
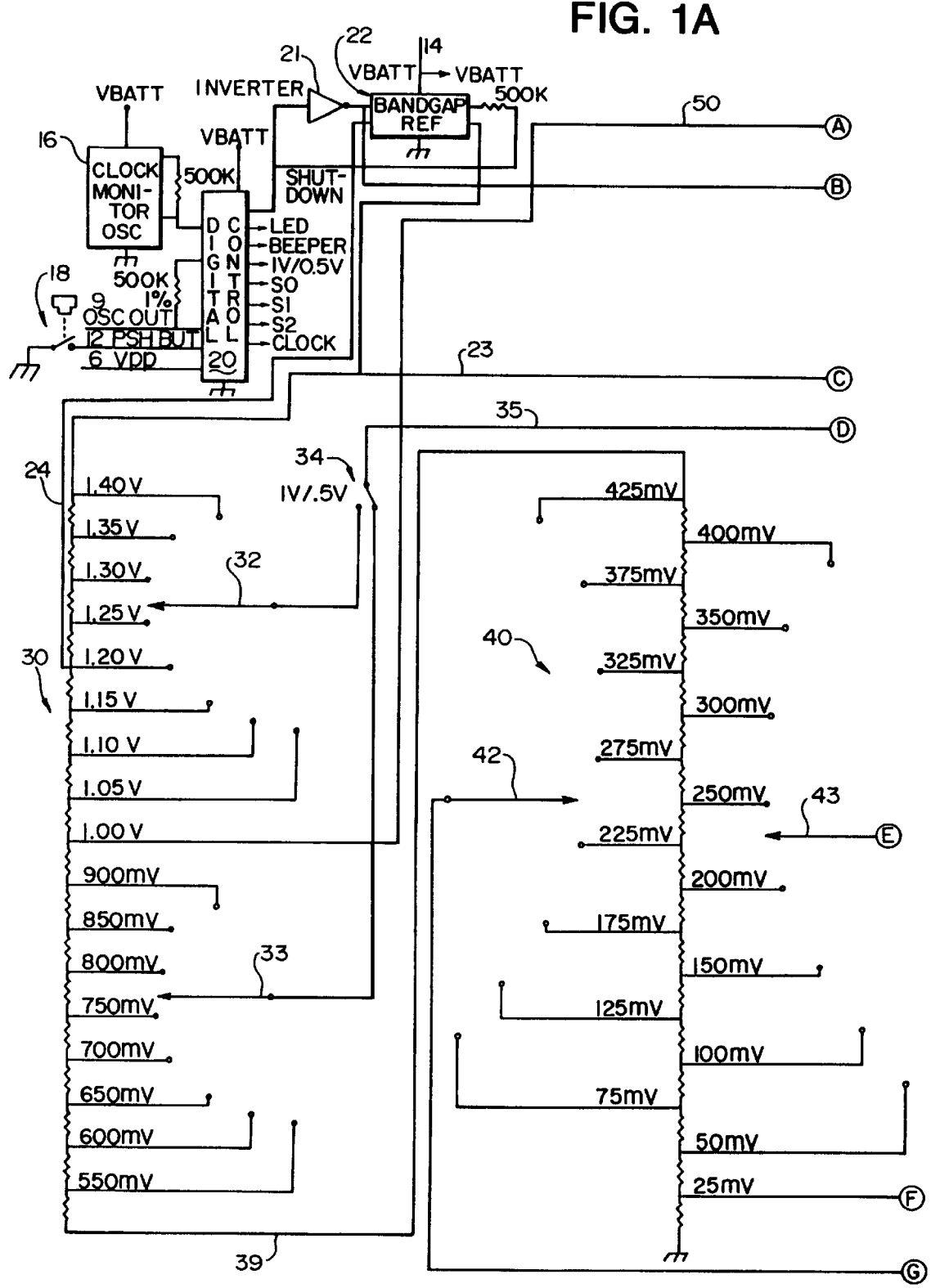
FIG. 1, consisting of parts 1A, 1B, and 1C, is a circuit diagram of a preferred embodiment of the invention.

The present invention provides an improved electrotransport delivery device for delivering a beneficial agent (eg, a drug) to a patient. When used in this context herein, the term "agent" refers to beneficial agents, such as drugs, within the class which can be delivered through body surfaces. The expression "drug" is intended to have a broad interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention can also be used to deliver polypeptides, proteins, and other macromolecules. These macromolecular substances typically have a molecular weight of at least about 300 daltons, and more typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (eg, HGH, HMG, HCG, desmopressin acetate, etc), follicle luteoids, $\alpha$ANF, growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, prostaglandin antagonists, pentigetide, protein C, protein S, renin inhibitors, thymosin alpha-1, thrombolytics, TNF, vaccines, vasopressin antagonists, analogs, VIP, alpha-1 anti-trypsin (recombinant).

The invention has particular utility in the delivery of agents which are adapted to be delivered in a discontinuous fashion. Examples of these include delivery of LHRH to induce ovulation, delivery of insulin at meal times, delivery of an anti-migraine drug to treat migraines and following migraine episodes and/or cluster headaches, delivery of antidiarrheals to treat intermittent episodes of diarrhea, antinauseants to treat intermittent episodes of nausea, delivery of vasodilators to treat angina, among others. A particularly preferred use of the present invention is in patient-initiated electrotransport delivery of analgesics such as fentanyl, sufentanil, morphine or related compounds to control pain.

Figure 4:
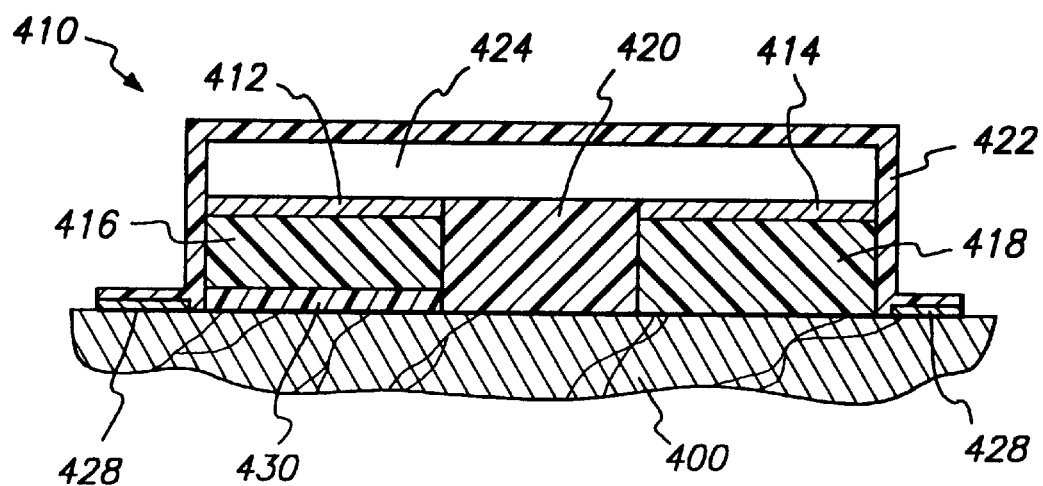
FIG. 4 is a sectional view of one embodiment of an electrotransport device which can be used with the present invention.

The control circuit and method of operating an electrotransport device according to the present invention are suitable for use in a wide variety of electrotransport devices. One example of an electrotransport drug delivery device which may be used with the present invention is designated by reference numeral 410 and is illustrated in FIG. 4. Device 410 has two current conducting members, referred to herein as a donor electrode 412 and a counter electrode 414. The electrodes 412 and 414 may be composed of an electrically conductive material such as a metal. For example, the electrodes 412, 414 may be formed from metal foil, metal screen, metal deposited or painted on a suitable backing, such as by calendaring or film evaporation, or by mixing a conductive filler (eg, a metal powder, powdered graphite, carbon fibers, etc) in a binder matrix. Examples of suitable metals include silver, zinc, silver chloride, aluminum, platinum, stainless steel, gold, and titanium. Most preferably, the anodic electrode is comprised of silver, while the cathodic electrode is comprised of silver chloride. Silver is preferred as an anode over other metals because of its relatively low toxicity to humans. Silver chloride is preferred as a cathode because the reduction of silver chloride produces chloride ions which are endogenous to the human body.

The donor and counter electrodes 412 and 414 are positioned adjacent to the donor reservoir 416 and the counter agent reservoir 418, respectively. The donor reservoir 416 contains the agent to be delivered, while the counter reservoir 418 typically contains a biocompatible electrolytic salt. The donor reservoir 416 and optional counter agent reservoir 418 may be any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. More preferably, the matrices of the reservoirs 416 and 418 are composed, at least in part, of a hydrophilic polymer material. Hydrophilic polymers are preferred because water is the preferred ion transport medium, and hydrophilic polymers have a relatively high equilibrium water content. Most preferably, the matrices of the reservoirs 416 and 418 are solid polymer matrices composed, at least in part, of insoluble hydrophilic polymer. Insoluble hydrophilic polymer matrices are preferred for structural reasons over soluble hydrophilic polymers.

Both natural and synthetic hydrophilic polymers may be used. Suitable hydrophilic polymers include polyvinylpyrrolidones, polyvinyl alcohol, polyethylene oxides such as Polyox® manufactured by Union Carbide Corp.; Carbopol® manufactured by BF Goodrich of Akron, Ohio; blends of polyoxyethylene or polyethylene glycols with polyacrylic acid such as Polyox® blended with Carbopol®, polyacrylamide, Klucel®, cross-linked dextran such as Sephadex (Pharmacia Fine Chemicals, AB, Uppsala, Sweden), Water Lock® (Grain Processing Corp., Muscatine, Iowa) which is a starch-graft-poly(sodium acrylate-co-acrylamide) polymer, cellulose derivatives such as hydroxyethyl cellulose, hydroxylpropylmethylcellulose, low-substituted hydroxypropylcellulose, and cross-linked Na-carboxymethylcellulose such as Ac-Di-Sol (FMC Corp., Philadelphia, Pa.) hydrogels such as polyhydroxyethyl methacrylate (National Patent Development Corp.), natural gums, chitosan, pectin, starch, guar gum, locust bean gum, and the like, along with blends thereof. Of these, polyvinylpyrrolidones are preferred.

The reservoir matrices may be a polymeric matrix structure formed by blending the desired agent, electrolyte, or other component(s), with an inert polymer by such processes as melt blending, solvent casting, or extrusion. The counter reservoir 418 may contain any one or more of the following electrolytes: alkali metal salts such as NaCl; alkaline earth metal salts such as chlorides, sulfates, nitrates, carbonates, and phosphates; organic salts such as ascorbates, citrates, and acetates; electrolytes containing redox species such as $Cu^{-2}$, $Fe^{-2}$, $Fe^{-3}$, quinone, hydroquinone, $Ag^{-2}$ and $IO_3^-$; and other biocompatible salts and buffers. Sodium chloride is the preferred electrolytic salt for the counter reservoir 418. In addition to the agent to be delivered and electrolyte, the reservoirs 416 and 418 may also contain other conventional materials such as dyes, pigments, inert fillers, and the like.

The donor electrode 412 and donor reservoir 416 are separated from the counter electrode 414 and counter reservoir 418 by an electrical insulator 420 which prevents electrical shorting. The insulator 420 prevents direct ion transport, ie, short-circuiting, between the donor reservoir 416 or the donor electrode 412 and the counter electrode 414 or optional counter reservoir 418. Given the purpose of the insulator, insulator 420 is preferably made of a hydrophobic material which is impermeable to the passage of both ions and electrons. Preferably, the insulating material is a material capable of strong bonding with the reservoir polymers, thereby providing further overall structural integrity for the device. Preferred insulating materials include poly (isobutylenes) and ethylene vinyl acetates (EVA).

The device 410 also has a backing layer 422 composed of a water-proof and preferably electrically insulating material. In addition, the backing layer 422 may provide some structural integrity to the device.

Electrical power may be supplied by a current generating and control circuit, shown schematically in FIG. 4 as a layer 424, which may include one or more batteries. One or more 3 volt button cell batteries, such as PANASONIC® model CR 2025, are suitable to power device 410. The power source in layer 424 is in electrical contact with the electrodes 412 and 414 such that each of the electrodes 412, 414 is electrically connected to the opposite pole of the power source in layer 424. Layer 424 also includes electronic circuitry for controlling the operation of the electrotransport device 410 such that device 410 applies electrotransport current to the patient in a discontinuous manner. Thus, layer 424 may include circuitry designed to permit the patient to manually turn the system on and off, such as with an on-demand medication regime, or to turn the system on and off at some desired periodicity, for example, to match the natural or circadian patterns of the body. A relatively simple controller or microprocessor can control the current as a function of time or can generate complex current wave forms such as pulses or sinusoidal waves. The control circuitry may also include a biosensor and some type of feedback system which monitors biosignals, provides an assessment of therapy, and adjusts the drug delivery accordingly.

The device 410 adheres to the body surface 400 in this embodiment by means of a peripheral adhesive layer 428. An optional passive flux control membrane 430 is positioned between the body surface 400 and the donor reservoir 416, respectively.

The device 410 may additionally contain other features, such as a removable protective liner (not shown) on the body surface contacting face of the device. Furthermore, certain components in device 410 are unnecessary or optional. Counter reservoir 418 is one example of an optional component. Also, if electrodes 412 and 414 are chosen such that a galvanic couple exists, an independent power source, eg, one or more batteries, in layer 424 may be an optional component. Thus, device 410 of FIG. 4 is provided solely for illustration of one example of an electrotransport delivery device which may be used with the compositions of the present invention.

Figure 1C:
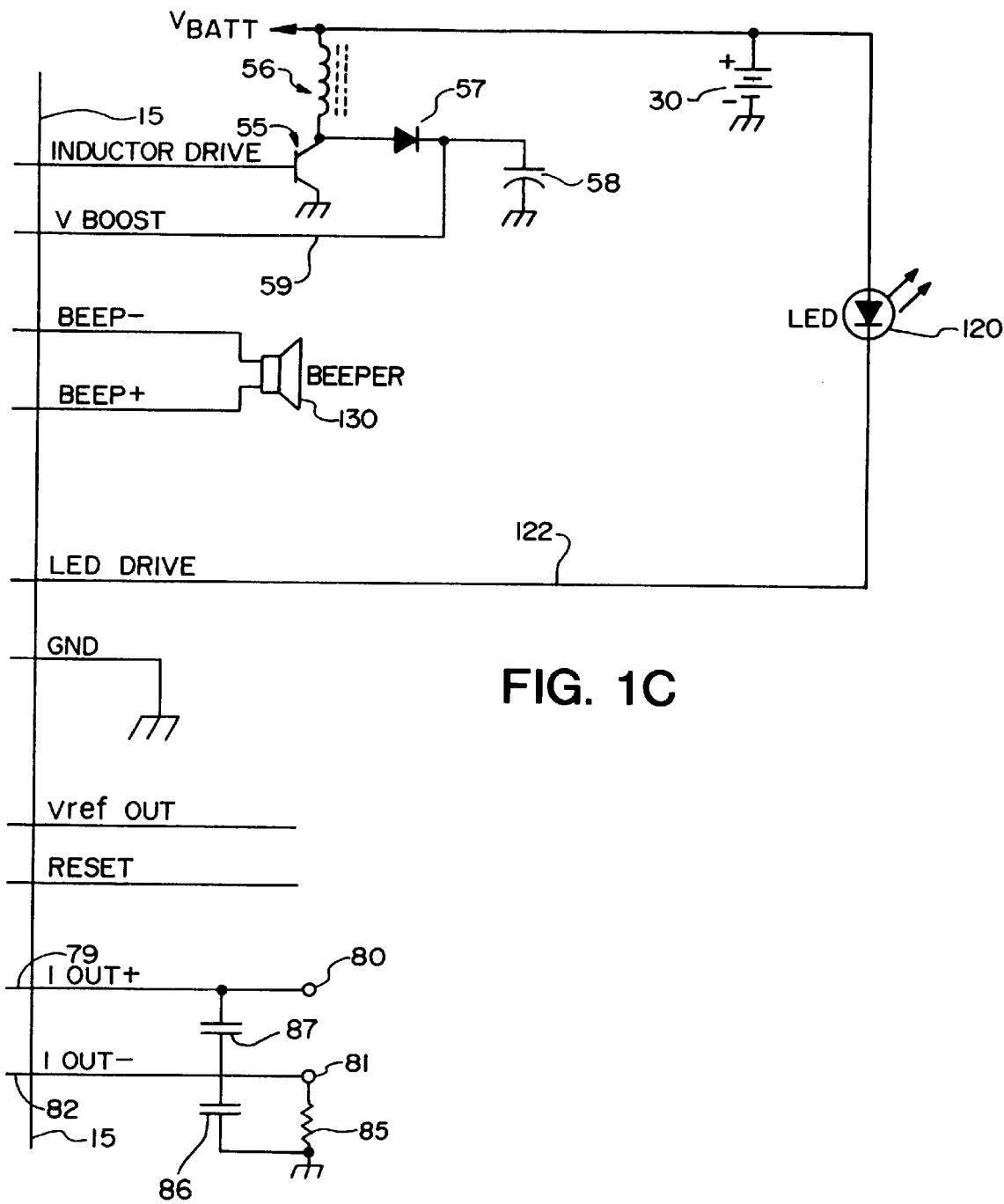
Figure 2A:
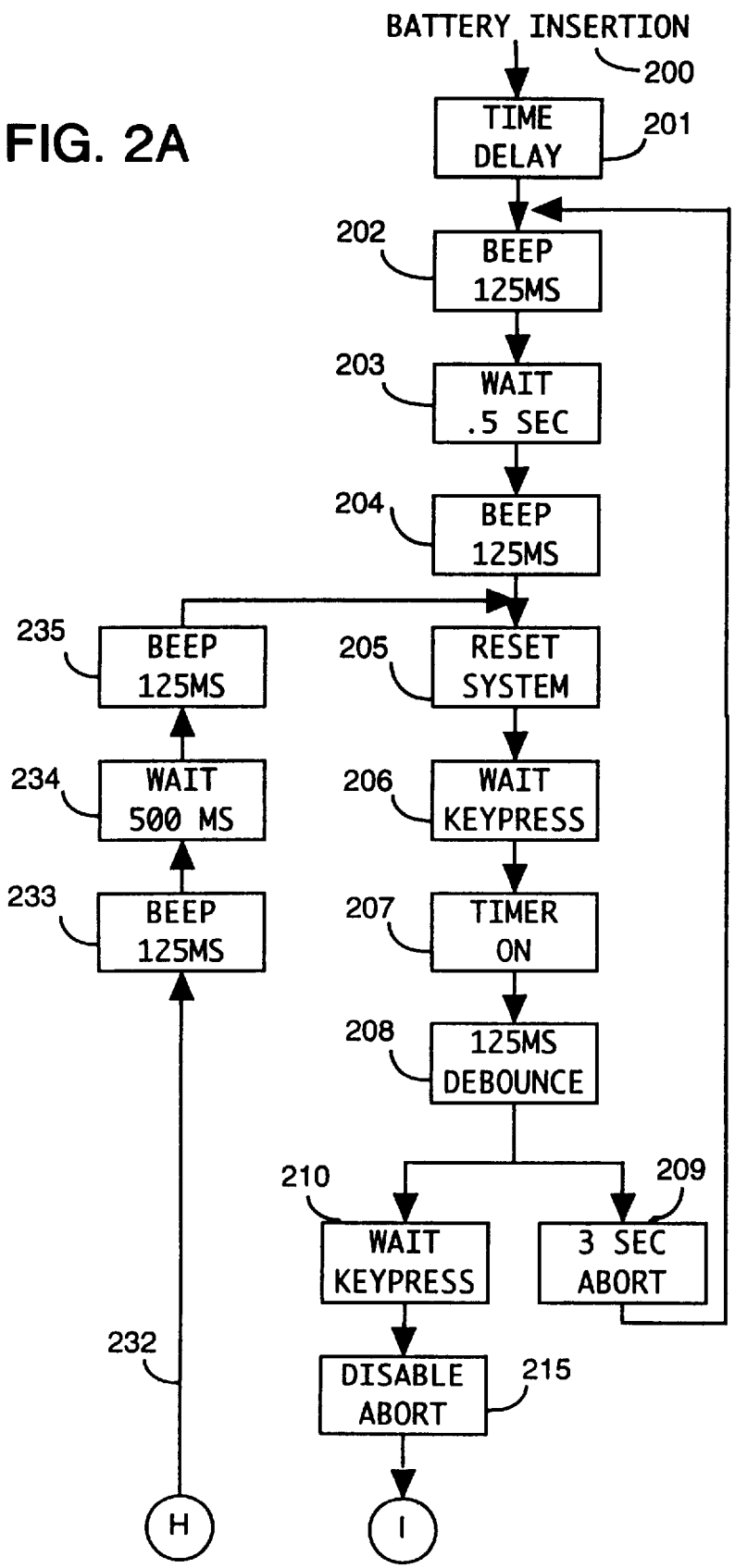
FIG. 2, consisting of parts 2A, 2B, 2C and 2D, is a flowchart illustrating the operation of the electrotransport device according to the present invention.
Figure 2B:
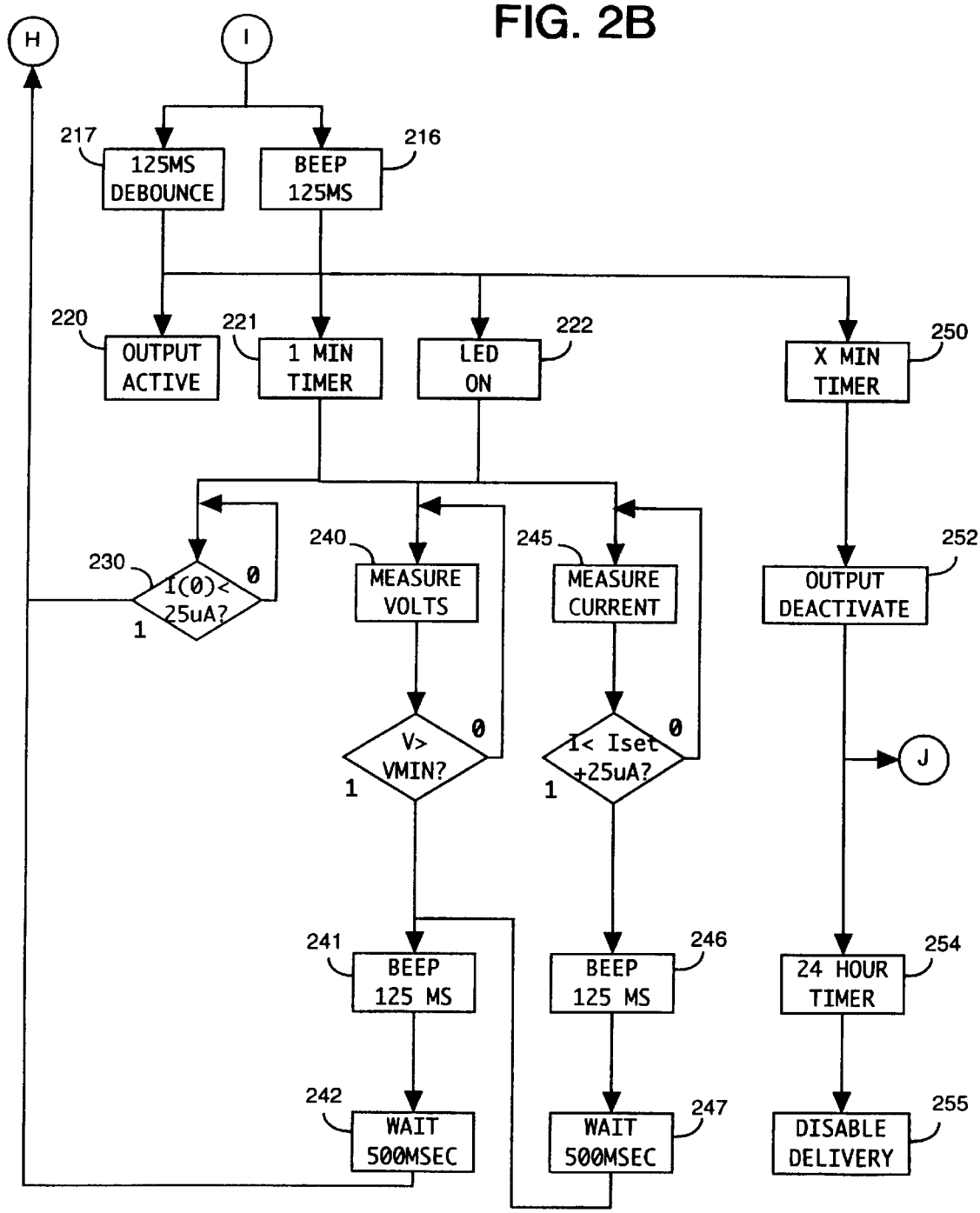
Figure 2C:
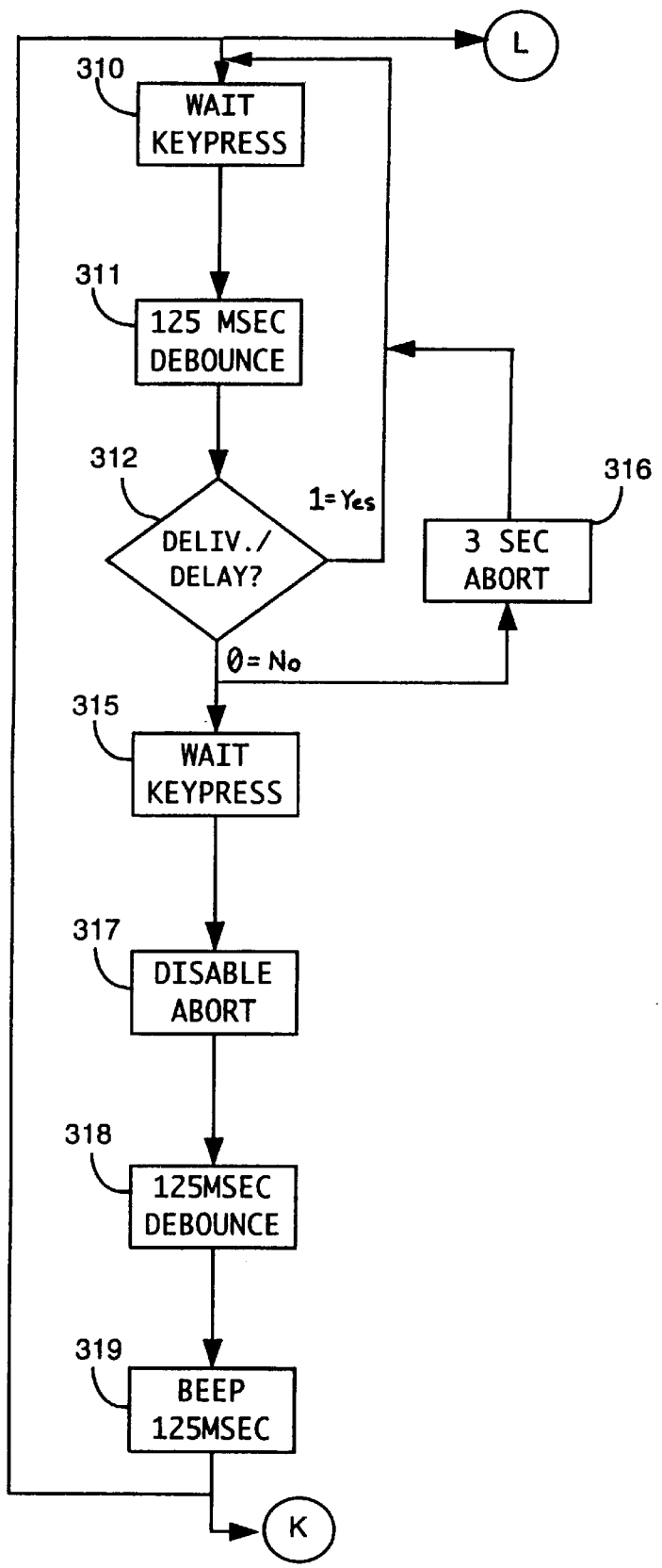
Figure 2D:
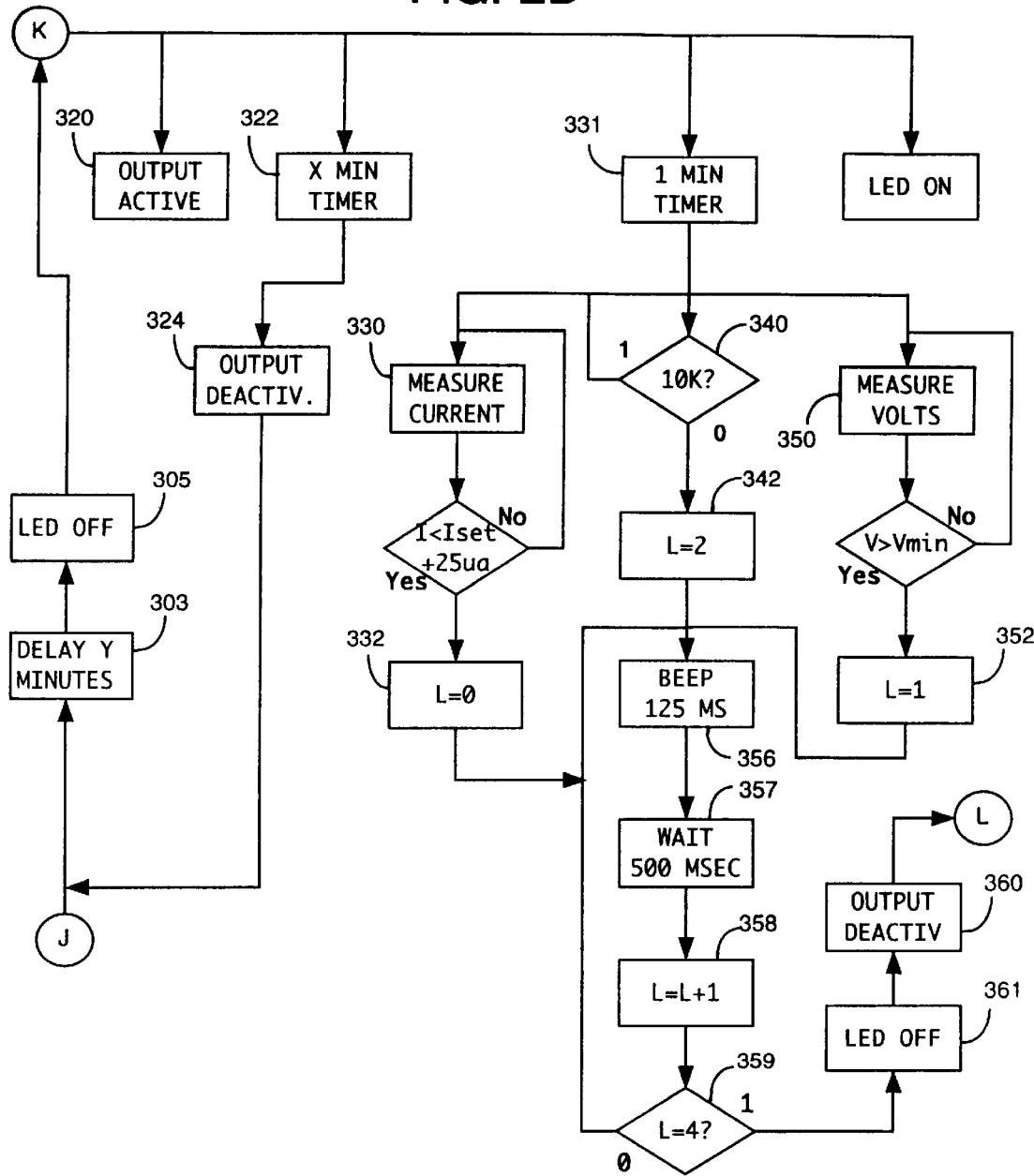

The preferred embodiment of the control system of the invention is implemented in an Application Specific Integrated Circuit (ASIC), although it will be appreciated from the following description of operation, that other technologies or devices could be used to implement the invention. With reference to FIGS. 1A–1C, all the components shown therein are implemented on the ASIC, with the exception of the components shown to the right of the ASIC boundary line 15 in FIG. 1C and the pushbutton switch 18 (FIG. 1A).

In practical implementation, as shown in FIG. 3, the ASIC 150, a battery, and a few components external to the ASIC including an inductor 56 for the voltage boost circuit, an LED indicator 120, a beeper 130, a pushbutton switch 18 are all mounted on a circuit board 141 and housed in a housing 140, 142 adapted to be worn by the patient. Circuit board 141 is held between the top housing 140 and the bottom housing 142. Bottom housing 142 includes recesses formed therein to receive electrodes 143 and 144, which connect to output terminals 80, 81 of the circuit. Gels 145 and 146, one of which contains the agent to be delivered and the other of which contains a biocompatible electrolyte salt (eg, NaCl), are in contact with electrodes 143, 144, respectively, in the recesses 147, 149, respectively, in the bottom housing 142. Adhesive layer 148 is at the bottom or skin contact side of the electrotransport delivery device, for attachment to the patient's skin to hold the device in place with the gels 145, 146 in contact with the skin. Pushbutton switch 18 is accessible on the outside of the top housing 140, and LED 120 is mounted to be visible to the user, through an aperture provided in the top housing 140.

As seen in FIG. 1A, pushbutton switch 18 connects to a digital control 20. Many of the functions of the device are coordinated by digital control 20, as explained below with reference to the flowchart of FIG. 2. Digital control 20 includes a number of outputs for operating and controlling various aspects of the circuit, indicated in FIG. 1A as SHUTDOWN, LED, BEEPER, 1V/0.5V, S0, S1, S2, and CLOCK. The clock signal enables the clock monitor oscillator 16, which receives an operating voltage from VBATT (as do numerous other circuits indicated in the figure), to provide output clock signals to an input of digital control 20.

An oscillator output is provided on pin 9 from digital control 20 as a test point, and pin 6 provides an input Vpp for high voltage to configure EPROM cells.

Reference number 22 designates a bandgap reference generating circuit. This circuit operates on VBATT, and produces a stable regulated reference voltage which is used for generating needed bias voltages within the ASIC, and also for setting references which are used by the current output and the monitoring circuits therefor. Specifically, bandgap reference 22 produces a reference voltage on lead 23, one branch of which goes to a bias generator 26 (FIG. 1B). This circuit produces reference bias voltages labelled BIAS 1–BIAS 7 which are used by various other parts of the circuit as indicated.

Another branch of lead 23 connects to a voltage divider 30 (FIG. 1A). Voltage divider 30 includes a number of intermediate voltage taps, indicated as varying from 1.40V to 550 mV. The taps from 1.05V to 1.40V are selectable by a switch 32. The voltage taps from 550 mV to 900 mV are selectable by a switch 33. Switches 32 and 33 are in turn selected by a switch 34 so that the selected reference voltage from switch 32 or 33 is provided on lead 35. This voltage is used for monitoring for UNDER VOLTAGE as explained below.

From the bottom of voltage divider 30, a lead 39 connects to another voltage divider 40. Voltage divider 40, whose bottom terminal connects to ground, provides voltage taps ranging from 25 mV to 425 mV, in 25 mV intervals.

Alternate taps are selectively connected to a switch 42, and alternate taps are connected to a switch 43. Switches 42 and 43 are operated together, so that pairs of adjacent voltages are selected respectively by switch 42 and 43. These pairs of voltages are used for setting the output current and the overcurrent reference, as explained further below.

The switch devices 32, 33, 34, 42, 43 are represented in FIG. 1A as switches, but are implemented in the ASIC as EPROM selected transmission gates which switch values through transistors. The settings for these devices are set by EPROM programming at the factory, during a testing phase prior to encapsulation of the die for the ASIC. The die has a number of pads used for testing and programming which are accessible prior to encapsulation, but which are not brought out as leads in the finished ASIC. In programming, a logic code for a desired transmission gate switch setting is placed on the appropriate die pads, and the high voltage Vpp is pulsed at pin 6. This is repeated for each of the switch settings needed. Also, settings for the desired dosage time interval and lockout time interval, discussed below, are also programmed into the ASIC using EPROM programming techniques. Normally all devices to be produced would have the same programmed values. However, the programmability feature provides advantages during development and testing of devices, and provides the ability to produce different models of devices, using the same die design.

The 1.20V reference from voltage divider 30 is conveyed on lead 24 back to bandgap reference 22, as a regulation reference for maintaining the voltages at the voltage dividers constant despite changes in the battery.

The SHUTDOWN output of digital control 20 connects through an invertor and also through a 500K resistor to bandgap reference 22. The SHUTDOWN output of digital control 20 disables the function of the bandgap reference 22 during a shutdown mode as explained below.

The 1.00V reference from voltage divider 30 is conveyed via lead 50 to circuitry which controls the generation of the boosted voltage, VBoost (See FIG. 1B), used by the output current generating portions of the circuit. Specifically, lead 50 connects to a comparator 51 (FIG. 1B) which in turn connects to a gate 52. Gate 52 also receives a clock input, and when enabled, provides pulses on lead 53 which is the inductor drive. As seen in FIG. 1C, this inductor drive connects through a transistor switch 55, whose collector connects through an inductor 56 to the VBATT voltage. The switching of transistor 55 produces high voltage pulses which are rectified and filtered by diode 57 and capacitor 58. The voltage provided on lead 59 is the boosted voltage Vboost used primarily by the output current generator. A branch of lead 59 also connects through a 500K resistor to an input of comparator 51, as a reference point. A portion of the Vboost voltage, (67K/500K+67K)*Vboost, is compared to the 1 volt reference, and pulses are supplied by the output of comparator 51 whenever its negative input is less than 1 volt. The shutdown signal from digital control 20, from invertor 21 is also applied to an input of gate 52, and to a switch 60, also connected to a 67K resistor to the negative input of comparator 51. The shutdown signal keeps the Vboost voltage from being generated unless a delivery has been started.

The voltage reference selected at switch 43 (FIG. 1A) is applied via lead E to the non-inverting input of operational amplifier 70 (FIG. 1B). This amplifier is also connected to receive bias voltages and VBOOST, and its output connects via lead 79 to the positive output current terminal 80 for the electrotransport delivery of the beneficial agent. Terminals 80 and 81 connect to the donor and counter electrodes of the device (eg, electrodes 143 and 144 of the device illustrated in FIG. 3). A 1 kilohm resistor 85 is connected from Output terminal 81 to signal ground. Lead 82 connects the negative output terminal 81 to a resistor 83, which connects by way of lead 84 to the inverting input of operational amplifier 70. Operational amplifier 70 and associated components thus form the output current drive and regulating functions of the device. Specifically, as a selected voltage is applied to operational amplifier 70 from selector switch 43, this causes the creation of a corresponding amount of output current, which is regulated by means of the feedback loop through the skin resistance and resistor 85 to the inverting input. Operational amplifier 70 thus controls whatever voltage is needed (within power supply VBOOST limits) to drive the selected output current.

Checks on output current and circuit performance, for minimum current, over current and undervoltage are provided by additional circuits. Comparator 90 (FIG. 1B) and associated circuitry monitors the voltage drop across the patient's skin and switches to prevent continued operation in the event of an undervoltage condition. Comparator 90 receives the voltage from lead 79, which is the + output current, at its inverting input, and receives a selected reference voltage from lead 35 at its noninverting input. The voltage at lead 35 is selected at the time of programming, to provide a safety margin of 0.5 volts or 1.0 volts across the skin, depending on the selection of switch 34 and the selection of switch 32 or 33. This value also takes into account the voltage drop across the 1K resistor 85, which also appears on lead 79. In typical normal operation, there might be a voltage of perhaps 1.5 volts across the skin. This circuit can check for a value of less than a predetermined voltage drop across the electrodes (eg, 0.5 volt) which would indicate a problem of too low impedance. Thus, for example, if the output current is set for 250 microamps, and the undervoltage is set at 0.5 volts (switch 34), then switch 33 will be programmed to 750 mV, which is the sum of the 0.5 volt margin plus the 250 mV drop across resistor 85. The output of comparator 90 will switch in an undervoltage condition, to provide an UNDER VOLTAGE signal to digital control 20.

Comparators 100 and 110 (FIG. 1B) are provided to indicate low and high output current. The feedback voltage from the lead 84 is applied to the inverting input of comparator 100 and the noninverting input of comparator 110. The noninverting input of comparator 100 receives a reference voltage from lead F, the 25 mV tap of voltage divider 40. This reference corresponds to a current through the output terminals 80, 81 of 25 microamps. The output of comparator 100 thus provides a signal indicating whether the output current is greater than or less than 25 microamps, which is used by the digital control 20.

Comparator 110 receives at its inverting input a reference voltage on lead G from the programmed select switch 42 of voltage divider 40. This reference is paired with the programmed reference selected by 43 for the output operational amplifier 70, such that comparator 110 is normally set for detecting an output current a predetermined amount, for example 25 microamps, greater than the selected output current. Comparator 110 thus provides an output signal which indicates if the actual output current exceeds the selected output current by a predetermined amount. This signal is also used by the digital control 20.

Digital control 20 also controls the LED 120 and Beeper 130 (FIG. 1C), which are used for providing various indications to the patient or health care personnel. The LED signal from digital control 20 is applied to an amplifier 121 (FIG. 1B), which receives bias and battery voltages. The output of amplifier 121 connects through lead 122 (FIG. 1C) to the cathode of LED 120, which is mounted in the housing so as to be visible. The anode of LED 120 connects to the battery voltage VBATT. This circuitry enables digital control 20 to turn LED 120 ON and OFF.

The BEEPER signal from digital control 20 connects to buffer amplifier 131 (FIG. 1B), and through invertor 132 to buffer amplifier 133. Outputs of these buffer amplifiers 131, 133 connect through the BEEP− and BEEP+ leads to the beeper 130 (FIG. 1C). This circuitry enables digital control 20 to selectively activate beeper 130.

The operation of the circuitry of FIGS. 1A–1C will now be explained with reference to the operational flowchart illustrated in FIG. 2. The device has previously been programmed, through EPROM programming, for the desired output current, the overcurrent limit, and also for the duration of a delivery, and the duration of the lockout interval. Operation begins upon initial battery insertion, indicated as step 200 in FIG. 2. A small time delay is provided at step 201 to allow start-up and settling of the circuit. Control then passes to step 202, which causes a beep of 125 milliseconds, followed by a 0.5 second wait, and another 125 ms beep at step 204. This double beep serves to confirm to the user that the system has responded to the insertion of the battery. The system is reset at step 205, and then the system waits at step 206 indefinitely for a keypress of pushbutton 18.

The system is designed to activate (ie, apply electrotransport current for a predetermined (eg, 10 minute) interval of time) upon the patient or other medical personnel depressing pushbutton 18 twice within a short predetermined period of time (eg, about 3 seconds) so as to avoid unintentional activation of the device caused by the patient inadvertently bumping or pressing pushing pushbutton 18. Upon the occurrence of a first keypress of pushbutton 18, a 3 second timer function is activated at step 207. After a 125 ms switch debounce interval represented by step 208, the system awaits a second keypress at step 210. If no second keypress occurs within the 3 second period, step 209 aborts the wait, and returns control to step 202. The system then goes through the startup again, and waits for a keypress at step 206.

If a second keypress is detected within 3 seconds, indicating that the user intends to initiate electrotransport drug delivery, control passes through debounce step 217 to step 220 to activate the output, having first initiated a confirming beep at step 216. At the same time the electrotransport current output is activated, a timer is started at step 221, and the LED 120 is activated at step 222 to signal that the system is operational and is delivering current/drug. As mentioned earlier, the electrical impedance of living biological membranes, such as human skin, tends to fluctuate during the first minute of so of application of electrotransport current. Thus, the timer started at step 221 is set to count at least about a 40 second, preferably at least about a 50 second, and most preferably about a 60 second period of time. During the first 1 minute or so of operation, the output current is allowed to start and to stabilize, because, as noted above, the skin impedance can widely fluctuate during the first minute or so of operation. After the approximately 1 minute period of time has elapsed, the system begins to simultaneously and continuously check three operating parameters, applied current (both too little and too much current) and voltage drop across the electrodes. The checking of these operating parameters is described in greater detail hereinafter.

CHECKING FOR UNDERCURRENT CONDITION

Step 230 continuously checks for too little current being applied, and therefore too little drug being delivered, to the patient. Such an undercurrent condition can occur if the electrodes/reservoirs are placed on heavily callused skin or skin having an unusually high impedance/resistance, or if the electrotransport current drive circuit has a malfunction. Step 230 checks the condition of comparator 100 (FIG. 1B), and if current is greater than 25 μA, control keeps looping through step 230. If the output current is less than the 25 μA level, control passes as indicated on path 232 to abort the delivery of electrotransport current. Two beeps are generated at steps 233–235 and control passes to step 205 to reset the system and await 2 successive keypresses to try again.

While the minimum current is being checked at step 230, the output voltage is being checked at step 240. This is done by comparator 90 (FIG. 1B). If the voltage drop (ΔV) across the electrodes is above the predetermined minimum levels, control continually loops back through step 240. If the voltage at the output is below the predetermined level (eg, 0.5 volt), control passes through beep 241 and delay 242 to path 232, previously described, to reset the system.

Similarly, step 245 continuously checks for too much current, and therefore too much drug, being applied to the patient. Such an overcurrent condition can occur if the electrodes/reservoirs are inadvertently placed on cut or abraded skin or if the electrotransport drive circuit has a malfunction. The overcurrent check is done by comparator 110 (FIG. 1B). If the current goes above the predetermined level plus 25 μA, control passes through beep 241 and delay 242 to path 232, previously described, to reset the system. Thus the occurrence of any of the conditions of undervoltage, undercurrent or overcurrent after the one minute transition interval, which indicate some type of problem, results in deactivation of the output and resetting of the system. Also, since the various beeps 246, 241, 233 and 235 are cumulative, the number of beeps actually emitted tells which of the three monitored parameters is off specification. Therefore, the user can wait for the one minute period after starting, and if there is a problem starting up, the number of beeps at the end of the one minute period will indicate the type of problem. It may be that the electrodes are not placed properly, and after adjustment, operation can be tried again by two keypresses.

At the same time that the output is activated at step 230, a timer is started at step 250. The step 250 timer controls the length of time over which the electrotransport current is applied. This time period will vary depending upon the particular drug being delivered, the desired concentration of drug in the patient's body, the therapeutic condition being treated, among others. In the specific example of electrotransport delivery of fentanyl (a narcotic analgesic) to control pain, the period of drug delivery is typically in the range of about 5 to 20 minutes. At the end of this delivery period, the output is automatically deactivated at step 252. This also starts a 24 hour timing function at step 254. At the end of 24 hours, the electrotransport current drive circuit is permanently disabled. This puts a definite limit to the use of the device, so that its abuse potential is limited.

The steps thus far described (which are generally on the left-hand side of the flowchart) are for the initial drug delivery event. For subsequent deliveries, control is governed by the steps described below (which are generally on the right-hand side of the flowchart). The operation for subsequent deliveries are generally the same as for the initial one, but with certain additional functions. These include interposing a lockout delay between deliveries, and the logging and reporting of dosages by the user.

After the output is deactivated at step 252, a lockout delay function is optionally initiated at step 303. This controls the length of a mandatory waiting period which follows each drug delivery period. The waiting period will vary depending upon the particular drug being delivered, the desired concentration of drug in the patient's body, the therapeutic condition being treated, among others. In the specific example of electrotransport delivery of fentanyl (a narcotic analgesic) to control pain, the waiting or lockout period will typically be up to about 30 minutes. The LED 120 is turned off at step 305, and control passes to step 310 to await a keypress of the pushbutton. After a keypress and debounce period 311, step 312 tests whether there is a delivery or a lockout delay in progress. If not, then control passes to step 315 for a second keypress indicating the user wishes to start another bolus delivery. If this occurs within the 3 second timing function of step 316, disabled in step 317, then control passes through a debounce 318 and beep 319, to activate the output at step 320. This also starts the dosage timing function 322, which is the same as 250, previously described. At the end of the dosage period, the output is deactivated at step 324, counter 301 is incremented, and another lockout delay 303 is set.

As the dosage delivery begins, LED 120 is turned on and 1 minute timer 331 begins. At the completion of that time, measurements of overcurrent, undercurrent and undervoltage are begun at steps 330, 340 and 350. If errors are detected by any of these, the output will be deactivated and the LED will be turned off at steps 360, 361. But first, a string of 2 to 4 beeps will be generated to indicate which of the monitoring functions detected the problem. This is done by loading a value for a variable L equal to 0, 1 or 2 at steps 332, 342 or 352, corresponding to the error detected, and looping through steps 356–359 to generate the corresponding number of beeps, then exiting to deactivate the output at step 360. From there, control returns to step 310 to await a keypress, and since the lockout timer has not been activated, the user can try another dosage, but if the problem persists, it will again be deactivated after the one minute time period.

The preprogrammed values for the circuit will be chosen according to the intended use. For example, in the case of the previously mentioned application for delivery of fentanyl, the unit is set for a current 250 μA, the overcurrent is set at 275 μA, the undervoltage (for ΔV set at 0.5 volts) is set at 750 mV, the delivery time is set for 10 minutes, and the lockout time is set at zero (ie, no lockout). It will be appreciated that these preprogrammed settings are by way of example only, and not by way of limitation of the scope of the invention, as other settings may and will be used for different applications.

It will be appreciated from the above circuit description and operation of the preferred embodiment that the present invention provides an improved electrotransport device, which provides improved monitoring over operating parameters of the agent delivery, and which is particularly adapted for patient-initiated delivery of doses, for example, of pain medication, within predetermined limitations of length of dosage and optional lockout interval between doses.

What is claimed is:

1. A method of controlling operation of a device for delivering an agent through a body surface of a patient by electrotransport, the device including a pair of electrodes for contacting the body surface, at least one of the electrodes containing the agent to be delivered, a source of electrical power, and a drive circuit for applying electrotransport current to the electrodes, the method comprising:

activating the drive circuit to initiate delivery of the electrotransport current;

monitoring the operation of the drive circuit after a transition time period, said transition time period starting with the initiation of delivery and said monitoring delayed until the end of the transition period; and deactivating the drive circuit only if the monitoring determines that the drive circuit is operating outside a predetermined operating limit after said transition period.

2. The method of claim 1, wherein the monitoring includes monitoring output electrotransport current and deactivating delivery if the current is below a predetermined value after said transition time period.

3. The method of claim 1, wherein the monitoring includes monitoring output voltage and deactivating said delivery if the voltage is below a predetermined value after said transition time period.

4. The method of claim 1, wherein the monitoring includes monitoring output electrotransport current and deactivating said delivery if the current is greater than a predetermined value after said transition time period.

5. The method of claim 1, wherein the monitoring includes monitoring output voltage and deactivating said delivery if the voltage is above a predetermined value after said transition time period.

6. The method of claim 1, wherein the drive circuit delivers electrotransport current to the electrodes in a discontinuous manner.

7. The method of claim 1, wherein the drive circuit, when activated, applies electrotransport current to the electrodes for a predetermined delivery interval.

8. The method of claim 7 further including preventing the initiation of a delivery of electrotransport current during a lockout interval following the delivery interval.

9. The method of claim 1 including manually activating the drive circuit.

10. The method of claim 1, wherein the body surface is human skin and the transition time period is at least about 40 to 60 seconds.

* * * * *